United States Patent [19]

Kuroda et al.

[11] Patent Number: 5,100,750

[45] Date of Patent: Mar. 31, 1992

[54] PHOTOCONDUCTOR FOR ELECTROPHOTOGRAPHY COMPRISES POLYCYCLO HETEROCYCLIC CHARGE TRANSPORT COMPOUND CONTAINING N AND S

[75] Inventors: Masami Kuroda; Youichi Nakamura; Noboru Furusho, all of Kawasaka, Japan

[73] Assignee: Fuji Electric Co., Ltd., Kanagawa, Japan

[21] Appl. No.: 334,156

[22] Filed: Apr. 6, 1989

[30] Foreign Application Priority Data

Apr. 26, 1988 [JP] Japan ............................. 63-103679

[51] Int. Cl.$^5$ .............................................. G03G 5/14
[52] U.S. Cl. ........................................ 430/72; 430/77;
430/58; 252/500; 548/465
[58] Field of Search ...................... 430/22, 77, 58;
548/465

[56] References Cited

U.S. PATENT DOCUMENTS

| | | | |
|---|---|---|---|
| 3,484,237 | 12/1969 | Shattuck et al. | 430/57 |
| 4,150,987 | 8/1979 | Anderson et al. | 430/58 |
| 4,353,971 | 3/1982 | Chang et al. | 430/58 |
| 4,385,106 | 6/1983 | Sakai | 430/58 |
| 4,448,868 | 12/1984 | Suzuki et al. | 430/58 |
| 4,565,761 | 5/1986 | Katagiri et al. | 430/83 |
| 4,629,670 | 10/1986 | Katagiri et al. | 430/58 |
| 4,673,630 | 8/1987 | Katagiri et al. | 430/72 |
| 4,677,045 | 1/1987 | Champ et al. | 430/72 |
| 4,731,315 | 3/1988 | Horie et al. | 430/58 |
| 4,839,252 | 2/1989 | Murata et al. | 430/59 |
| 4,861,691 | 6/1989 | Kuroda et al. | 430/59 |
| 4,861,692 | 11/1989 | Kuroda et al. | 430/59 |

FOREIGN PATENT DOCUMENTS

| | | |
|---|---|---|
| 2041490 | 8/1971 | Fed. Rep. of Germany . |
| 3208337 | 10/1982 | Fed. Rep. of Germany . |
| 47-10785 | 5/1972 | Japan . |
| 47-37543 | 8/1972 | Japan . |
| 59-182456 | 6/1984 | Japan . |
| 59-182457 | 10/1984 | Japan . |

OTHER PUBLICATIONS

Chemical Abstracts Service Registration No. 84-83-3.
Chemical Abstracts Service Registration No. 27329-60-8.
Chemical Abstracts Service Registration No. 7570-45-8.

*Primary Examiner*—J. David Welsh
*Attorney, Agent, or Firm*—Spencer & Frank

[57] ABSTRACT

A photoconductor for electrophotography comprises a novel organic compound as a charge transporting substance. The organic compounds is represented by the following general formula:

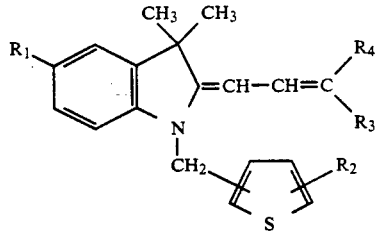

wherein, each of $R_1$ to $R_4$ stands for a hydrogen atom, a halogen atom, an alkoxy group, or an alkyl group, an aryl group, an alkenyl group, an aralkyl group, a thienyl group, each of which may have a substituent(s).

6 Claims, 1 Drawing Sheet

PHOTOCONDUCTOR FOR ELECTROPHOTOGRAPHY COMPRISES POLYCYCLO HETEROCYCLIC CHARGE TRANSPORT COMPOUND CONTAINING N AND S

BACKGROUND OF THE INVENTION

1. Field of the Invention

The present invention relates to photoconductors for electrophotography, and particularly to a photoconductor for electrophotography which contains a novel organic compound in the photosensitive layer thereof formed on an electroconductive substrate.

2. Description of the Prior Art

Photosensitive materials which have heretofore been used in photoconductors for electrophotography include inorganic photoconductive substances such as selenium and selenium alloys, dispersions of inorganic photoconductive substances such as zinc oxide and cadmium sulfide in resin binders, organic polymeric photoconductive substances such as poly-N-vinylcarbazole and polyvinylanthracene, organic photoconductive substances such as phthalocyanine compounds and bisazo compounds, and dispersions of such organic polymeric photoconductive substances in resin binders.

Photoconductors are required to have a function of maintaining a surface electric charge in the dark, a function of generating an electric charge upon receiving light, and a function of transporting an electric charge upon receiving light. They are classified into two types of photoconductors, namely so-called monolayer type photoconductors, and so-called laminate type photoconductors. The former comprises a single layer having all of the above-mentioned three functions, and the latter comprises functionally distinguishable laminated layers, one of which contributes mainly to the generation of electric charge, and another of which contributes to the retention of surface electric charge in the dark and the transportation of electric charge upon receiving light. In an electrophotographic method using a photoconductor of the kind as mentioned above, for example, the Carlson's system is applied to image formation. The image formation according to this system comprises steps of subjecting a photoconductor in the dark to corona discharge to charge the photoconductor, illuminating the surface of the charged photoconductor with imagewise light based on a manuscript or copy bearing, e.g., letters and/or pictures to form a latent electrostatic image, developing the formed latent electrostatic image with a toner, and transferring the developed toner image to a support such as a paper sheet to fix the toner image on the support. After the toner image transfer, the photoconductor is subjected to the steps of removal of the electric charge, removal of the remaining toner (cleaning), neutralization of the residual charge with light (erasion), and so on to be ready for reuse.

Photosensitive members for electrophotography in which use is made of organic materials have recently been put into practical use by virtue of the advantageous features of the organic materials such as flexibility, thermal stability, and/or a film forming capacity. They include a photoconductor comprising poly-N-vinylcarbazole and 2,4,7-trinitrofluoren-9-on (disclosed in U.S. Pat. No. 3,484,237), a photoconductor using an organic pigment as the main component (disclosed in Japanese Patent Laid-Open No. 37,543/1972), and a photoconductor using as a main component a eutectic complex composed of a dye and a resin (disclosed in Japanese Patent Laid-Open No. 10,785/1972). A number of novel hydrazone compounds have also been put into practical use for photoconductors.

Further, a variety of organic materials have been reported as a charge generating substance, which generates charge upon receiving light, such as a phthalocyanine compound, an azo compound or a pyrylium compound and as a charge transporting substance, which contributes to the transportation of a charge, such as a pyrazoline compound, a hydrazone compound, an oxazole compound or an oxaziazole compound. Photoconductors for electrophotography using these organic materials have been put into practical use.

Although organic materials have a number of advantageous features mentioned above with which inorganic materials are not endowed, however, the fact is that there have been obtained no organic materials fully satisfying all the characteristics required of a material to be used in photoconductors for electrophotography at the present. Particular problems involved in organic materials have been concerned with photosensitivity and characteristics in continuous repeated use.

SUMMARY OF THE INVENTION

An object of the present invention is to provide a photoconductor for electrophotography to be used in copying apparatuses and printers which photoconductor has a high photosensitivity and excellent characteristics in repeated use, through the use, in the photosensitive layer, of a novel organic materials not used to date as a charge transporting substance.

In the first aspect of the present invention, a photoconductor for electrography comprises:
a substrate; and
a photosensitive layer formed on the substrate and including at least one organic compound represented by the following general formula (I) as a charge transporting substance:

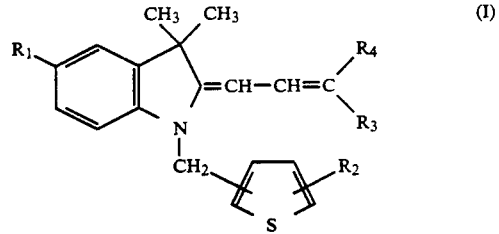

(I)

wherein, each of $R_1$ to $R_4$ stands for a hydrogen atom, a halogen atom, an alkoxy group, or an alkyl group, an aryl group, an alkenyl group, an aralkyl group, a thienyl group, each of which may have a substituent(s).

Here, the photosensitive layer may comprise a layer including a dispersion of a charge generating substance and a charge transporting substance selected from the organic compounds represented by the general formulae (I) in a binder resin.

The photosensitive layer may comprise a laminate of a charge transporting layer including a charge transporting substance selected from the organic compounds represented by the general formulae (I) and a charge generating layer. In the second aspect of the present invention, a photoconductor for electrophotography comprises:

a substrate; and a photosensitive layer formed on the substrate and including at least one organic compound represented by the following general formula (II) as a charge transporting substance:

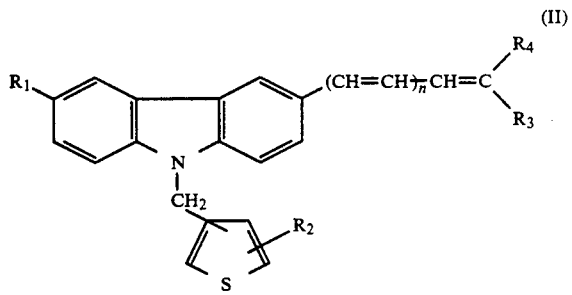

wherein, each of $R_1$ to $R_4$ stands for a hydrogen atom, a halogen atom, an alkoxy group, or an alkyl group, an aryl group, a thienyl group, an alkenyl group, an aralkyl group, each of which may have a substituent(s), n stands for an integer 0 or 1.

Here the photosensitive layer may comprise a layer including a dispersion of a charge generating substance and a charge transporting substance selected from the organic compounds represented by the general formulae (II) in a binder resin.

The photosensitive layer may comprise a laminate of a charge transporting layer including a charge transporting substance selected from the organic compounds represented by the general formulae (II) and a charge generating layer.

The above and other objects, effects, features and advantages of the present invention will become more apparent from the following description of embodiments thereof taken in conjunction with the accompanying drawings.

DETAILED DESCRIPTION OF PREFERRED EMBODIMENTS

Figure 1:
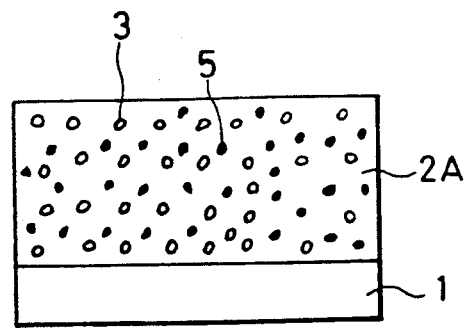
FIGS. 1 to 3 are schematic cross-sectional views of photoconductors according to the present invention, respectively.
Figure 2:
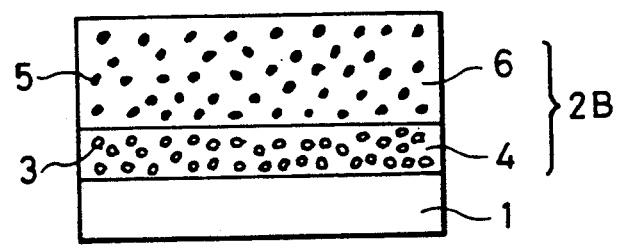
Figure 3:
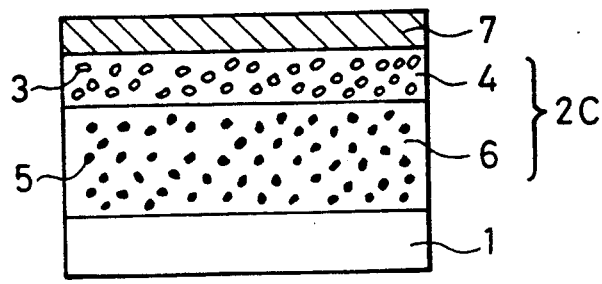

FIGS. 1, 2 and 3 are schematic cross-sectional views of different embodiments of the photoconductor of the present invention, respectively.

FIG. 1 shows a monolayer type photoconductor. A photosensitive layer 2A is provided on an electroconductive substrate 1. The photosensitive layer 2A comprises a charge generating substance 3 and a novel organic compound according to the present invention as a charge transporting substance 5 both of which substances are dispersed in a resin binder matrix so that the photosensitive layer 2A functions as photoconductor.

FIG. 2 shows a laminate type photoconductor. A laminated photosensitive layer 2B is provided on an electroconductive substrate 1, a lower layer of the laminate is a charge generating layer 4 including a charge generating substance 3 as the main component and an upper one is a charge transporting layer 6 containing a charge transporting substance 5 according to the present invention, so that the photosensitive layer 2B functions as a photoconductor. This photoconductor is usually used according to the negative charge mode.

FIG. 3 shows another laminate type photoconductor having a layer structure in reverse to that of FIG. 2. A laminated photosensitive layer 2C is provided on an electroconductive substrate 1, a lower layer of the laminate is a charge transporting layer 6 including a novel organic compound as a charge transporting substance 5 in accordance with the present invention and an upper one is a charge generating layer 4 including a charge generating substance 3. The photosensitive layer also functions as a photoconductor. This photoconductor is usually used according to the positive charge mode. In this case, a covering layer 7 may generally be further provided as shown in FIG. 3 to protect the charge generating layer 4.

Thus, there are two different types of layer structures in the photoconductor. The reason for this is that, even if any photoconductor with the layer structure as shown in FIG. 2 is to be used in the positive charge mode, no charge transporting substances adaptable to the positive charge mode have been found yet. Accordingly, when the positive charge mode is adapted, the photoconductor is required of a layer structure as shown in FIG. 3 at present.

A photoconductor as shown in FIG. 1 can be produced by dispersing a charge generating substance in a solution of a charge transporting substance and a resin binder and applying the resulting dispersion on an electroconductive substrate.

A photoconductor as shown in FIG. 2 can be prepared by depositing a charge generating substance on an electroconductive substrate by means of vacuum evaporation or applying and drying a dispersion of a particulate charge generating substance in a solvent and/or a resin binder on an electroconductive substrate, followed by applying a solution of a charge transporting substance and a resin binder on the resulting layer and drying.

A photoconductor as shown in FIG. 3 can be prepared by applying and drying a solution of a charge transporting substance and a resin binder on an electroconductive substrate, and depositing a charge generating substance on the resulting coating layer by means of vacuum evaporation or coating and drying a dispersion of a particulate charge generating substance in a solvent and/or a resin binder on the coating layer, followed by formation of a covering layer.

The electroconductive substrate 1 serves as an electrode of the photoconductor and as a support for a layer(s) formed thereon. The electroconductive substrate may be in the form of a cylinder, a plate or a film, and may be made of a metallic material such as aluminum, stainless steel or nickel, or other material having a surface treated to be electroconductive, such as glass so treated or a resin so treated.

The charge generating layer 4 is formed by application of a dispersion of a particulate charge generating substance 3 in a resin binder or by deposition of a charge generating substance by means of vacuum evaporation, or the like technique as described above, and this layer generates an electric charge upon receiving light. It is important that the charge generating layer 4 be high not only in charge generating efficiency but also in capability of injecting the generated electric charge into the charge transporting layer 6 and any covering layer 7, whose capability is desirably as little dependent upon the electric field as possible and high even in low intensity electric fields. Usable charge generating substances include phthalocyanine compound such as metal-free phthalocyanine and titanyl phthalocyanine; various azo, quinone and indigo pigments; dyes such a cyanine, squarylium, azulenium, and pyrylium compounds; and selenium and selenium compounds. Among them, a suitable compound can be chosen depending on the wavelength range of a light source used for the image formation. The thickness of the charge generating layer is determined depending on the extinction coefficient of a charge generating substance to be used therein in view of the layer's function of generating an electric charge, but is generally 5 μm or smaller, preferable 1 μm or smaller. It also is possible to form a charge generating layer using a charge generating substance as a main component in mixture with a charge transporting substance and so on. Resin binders usable in the charge generating layer include polycarbonates, polyesters, polyamides, polyurethanes, epoxy resins, silicone resins, and methacrylate homopolymer and copolymers, which may be used either alone or in an appropriate composition ratio.

The charge transporting layer 6 is a coating film containing an organic charge transporting substance in a resin binder. The charge transporting layer serves as an insulator layer in the dark so as to retain the electric charge of the photoconductor, and fulfills a function of transporting an electric charge injected from the charge generating layer upon receiving light. Resin binders usable in the charge transporting layer include polycarbonates, polyesters, polyamides, polyurethanes, epoxy resins, silicone resins, and methacrylate homopolymer and copolymers.

The covering layer 7 has a function of receiving and retaining an electric charge generated by corona discharge in the dark and a capability of transmitting light to which the charge generating layer should respond. It is necessary that the covering layer transmits light upon exposure of the photoconductor and allows the light to reach the charge generating layer, and then undergoes the injection of an electric charge generated in the charge generating layer to neutralize and erases a surface electric charge. Materials usable in the covering layer include organic insulating film-forming materials such as polyesters and polyamides. Such organic materials may also be used in mixture with an inorganic material such as a glass resin or $SiO_2$, or a material for lowering electric resistance such as a metal or a metallic oxide. Materials usable in the covering layer are not limited to organic insulating materials for film-forming, and further include inorganic materials such as $SiO_2$, metals, and metallic oxides, which may be formed into a covering layer by an appropriate method such as vacuum evaporation and deposition, or sputtering. From the viewpoint of the aforementioned description, it is desirable that the material to be used in the covering layer be as transparent as possible in the wavelength range in which the charge generating substance attains maximum light absorption.

Although the thickness of the covering layer depends on the material or composition thereof, it can be arbitrarily set in so far as it does not produce any adverse effects including an increase in a residual potential in continuous repeated use.

The charge transporting substances in accordance with the present invention include two groups.

The first group of organic compounds to be used in the present invention is represented by the following general formula (I).

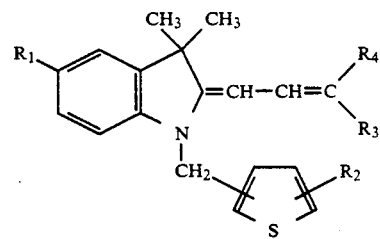

Wherein, each of $R_1$ to $R_4$ stands for a hydrogen atom, a halogen atom, an alkoxy group, or an alkyl group, an aryl group, an alkenyl group, an aralkyl group, a thienyl group, each of which may have a substituent(s).

The compounds represented by the general formula (I) can be synthesized by the reaction of an aldehyde of the formula:

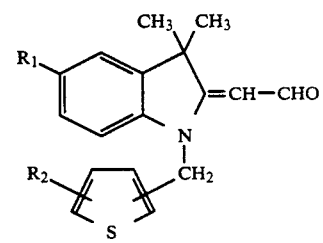

with a compound of the formula:

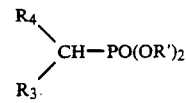

in an appropriate organic solvent such as N, N-dimethylformamide in the presence of an alkali under nitrogen flow.

When a part of the general formula (I) is specified, the following two general formulae (IA) and (IB) are obtained:

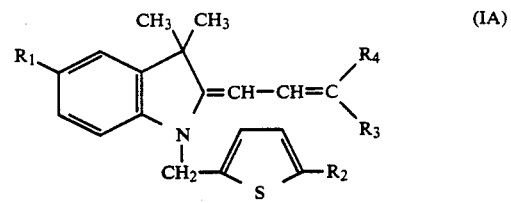

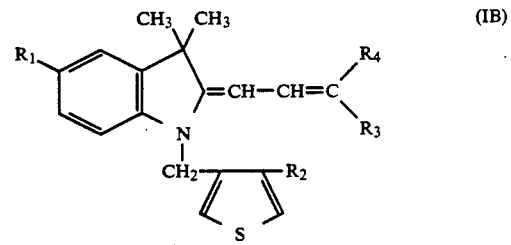

Further, when $R_1$, $R_2$, $R_3$ and $R_4$ are specified, specific examples are given. Tables 1 and 2 show specific examples of the compounds represented by the formulae (IA) and (IB).

TABLE 1

| Compound No. | $R_1$ | $R_2$ | $R_3$ | $R_4$ |
|---|---|---|---|---|
| I-1 | H | H | Ph | H |
| -2 | H | H | Ph | $CH_3$ |
| -3 | H | H | Ph | $C_2H_5$ |
| -4 | H | H | Ph | Ph |
| -5 | H | Br | Ph | H |
| -6 | H | H | 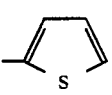 | H |
| -7 | H | H | 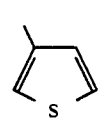 | H |
| -8 | Cl | H | Ph | H |
| -9 | $CH_3$ | H | Ph | $CH_3$ |
| -10 | $OCH_3$ | $CH_3$ | Ph | $C_2H_5$ |
| -11 | Br | H | Ph | $CH_3$ |
| -12 | Br | Br | Ph | $CH_3$ |
| -13 | Cl | Ph | Ph | Ph |
| -14 | Br | Br | Ph | Ph |

TABLE 2

| Compound No. | $R_1$ | $R_2$ | $R_3$ | $R_4$ |
|---|---|---|---|---|
| I-15 | H | H | Ph | H |
| -16 | H | H | Ph | $CH_3$ |
| -17 | H | H | Ph | Ph |
| -18 | H | H | Ph | $C_2H_5$ |
| -19 | H | Ph | Ph | $CH_3$ |
| -20 | $CH_3$ | Ph | Ph | Ph |
| -21 | Cl | $CH_3$ | Ph | $CH_3$ |
| -22 | Br | H | Ph | Ph |
| -23 | $OCH_3$ | H | Ph | $C_2H_5$ |
| -24 | H | H | 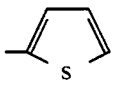 | H |
| -25 | H | H | 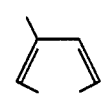 | H |
| -26 | H | $CH_3$ | Ph | $CH_3$ |
| -27 | H | Ph | Ph | Ph |
| -28 | H | $CH_3$ | Ph | Ph |

The second group of organic compounds to be used in the present invention is represented by the following general formula (II):

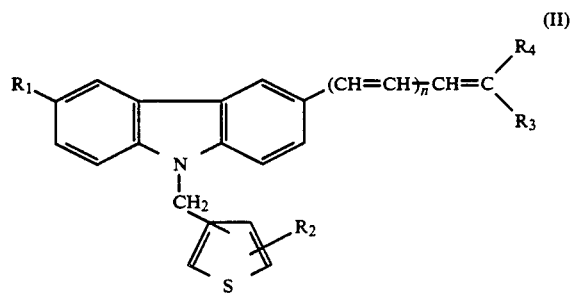

(II)

Wherein, each of $R_1$ to $R_4$ stands for a hydrogen atom, a halogen atom, an alkoxy group, or an alkyl group, an aryl group, a thienyl group, an alkenyl group, an aralkyl group, each of which may have a substituent(s), and n stands for an integer 0 to 1.

The compounds represented by the general formula (II) can be synthesized by the reaction of an aldehyde compound of the formula:

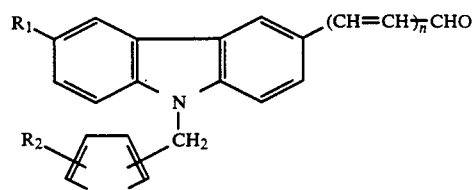

with a compound of the formula:

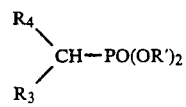

in an appropriate organic solvent such as N, N-dimethylformamide in the presence of an alkali under nitrogen (II).

When a part of the general formula (II) is specified, the following two general formulae (IIA) and (IIB) are obtained:

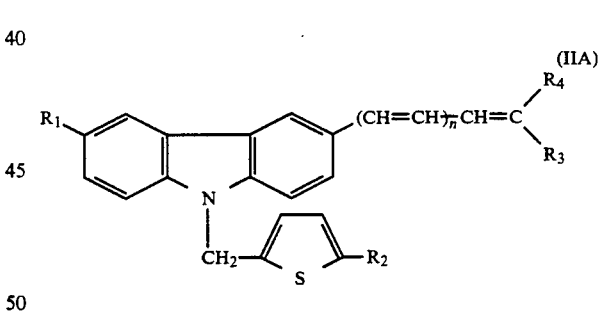

(IIA)

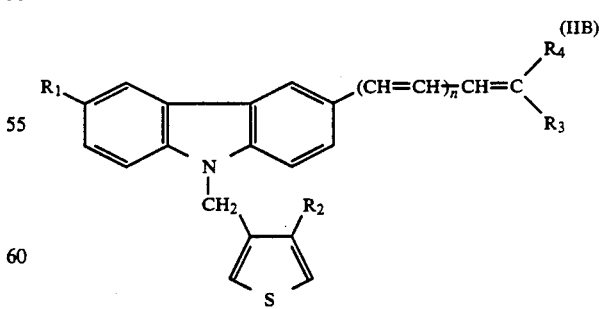

(IIB)

Further, when $R_1$, $R_2$, $R_3$ and $R_4$ are specified, specific examples are given. Table 3 and 4 show specific examples of the compounds represented by the formulae (IIA) and (IIB).

TABLE 3
(No. 1)
| Compound No. | n | R₁ | R₂ | R₃ | R₄ |
|---|---|---|---|---|---|
| II-1 | 0 | H | H | 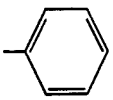 | H |
| -2 | 0 | H | H | 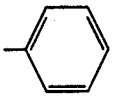 | CH₃ |
| -3 | 0 | H | Br | 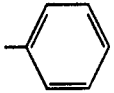 | C₂H₅ |
| -4 | 0 | H | H | 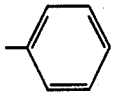 | 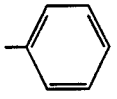 |
| -5 | 0 | Cl | H | 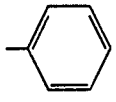 | CH₃ |
| -6 | 0 | Br | H | 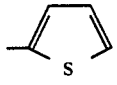 | H |
| -7 | 0 | CH₃ | 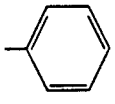 | 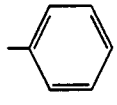 | C₂H₅ |
| -8 | 0 | OCH₃ | Br | 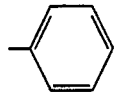 | 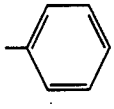 |
| -9 | 1 | H | H | 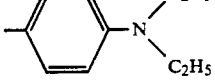 | H |
| -10 | 1 | H | H | 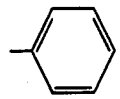 | CH₃ |
| -11 | 1 | H | H | 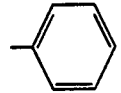 | C₂H₅ |
| II-12 | 1 | H | H | 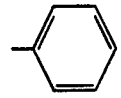 | 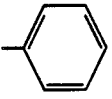 |
| -13 | 1 | OCH₃ | H | 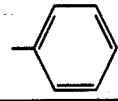 | CH₃ |

TABLE 4
(No. 1)

| Compound No. | n | R₁ | R₂ | R₃ | R₄ |
|---|---|---|---|---|---|
| II-14 | 0 | H | H | -C₆H₄-N(C₂H₅)₂ (para) | H |
| -15 | 0 | H | H | phenyl | CH₃ |
| -16 | 0 | H | H | phenyl | C₂H₅ |
| -17 | 0 | H | H | phenyl | phenyl |
| -18 | 0 | H | H | 2-thienyl | H |
| -19 | 0 | Br | H | phenyl | CH₃ |
| -20 | 0 | OCH₃ | CH₃ | phenyl | phenyl |
| II-21 | 0 | CH₃ | phenyl | phenyl | C₂H₅ |
| -22 | 1 | H | H | phenyl | phenyl |
| -23 | 1 | H | CH₃ | phenyl | CH₃ |
| -24 | 1 | Cl | H | phenyl | C₂H₅ |
| -25 | 1 | OCH₃ | H | phenyl | phenyl |
| -26 | 1 | Br | H | phenyl | phenyl |

Example will now be given, wherein various compounds represented by the general formula (I) or (II) were respectively used to produce photoconductors.

EXAMPLE 1

50 parts by weight of metal-free phthalocyanine (manufactured by Tokyo Kasei Co., Ltd.) pulverized with a ball mill for 150 hours and 100 parts by weight of the compound No. I-1 shown in Table 1 were kneaded together with 100 parts by weight of a polyester resin (Vylon 200 (trademark), manufactured by Toyobo Co., Ltd.) and tetrahydrofuran (THF) as a solvent with a mixer for 3 hours to prepare a coating liquid. The coating liquid was applied on an aluminum-deposited polyester film (Al-PET) as an electroconductive substrate by means of the wire bar technique to form a photosensitive layer having a dry thickness of 15 μm. Thus, a photoconductor with the structure shown in FIG. 1 was produced.

EXAMPLE 2

A photoconductor was produced by forming a photosensitive layer in the same manner as in Example 1 except that the compound No. II-1 shown in Table 3 was used instead of the compound No. I-1 in Example 1.

EXAMPLE 3

Metal-free α-phthalocyanine as a starting material was pulverized for 20 minutes into a fine powder with a pulverizer, a LIMMAC (Linear Induction Motor Mixing and Crushing manufactured by Fuji Electric Co., Ltd.) wherein a non-magnetic can containing the metal-free α-phthalocyanine and Teflon pieces as small acting pieces was placed between two linear motors faced each other. The sample of 1 part by weight of the fine powder thus prepared was dispersed in 50 parts by weight of DMF (N, N-dimethylformamide) as a solvent by means of an ultrasonic dispersion treatment. Thereafter, the sample was separated from DMF by filtration and dried to complete the treatment of metal-free phthalocyanine.

A solution of 100 parts by weight of the hydrazone compound No. I-2 shown in Table 2 in 700 parts by weight of tetrahydrofuran (THF) was mixed with a solution of 100 parts by weight of polymethyl methacrylate (PMMA, manufactured by Tokyo Kasei Co., Ltd.) in 700 parts by weight of toluene to prepare a coating liquid. The coating liquid was applied on an aluminum-deposited polyester film substrate by means of the wire bar technique to form a charge transporting layer having a dry thickness of 15 μm. 50 parts by weight of metal-free phthalocyanine treated in the above-mentioned manner, and 50 parts by weight of a polyester resin (Vylon 200), were kneaded with a mixer for 3 hours together with THF as a solvent to prepare a coating liquid, which was then applied on the charge transporting layer by the wire bar technique to form a charge generating layer having a dry thickness of 1 μm. Thus, a photoconductor with a structure corresponding to that shown in FIG. 3 was produced. A covering layer was not provided because it was not directly related to the present invention.

EXAMPLE 4

A photoconductor was produced by forming a photosensitive layer in the same manner as in Example 3 except that the compound No. II-2 shown in Table 3 was used instead of the compound No. I-2 in Example 3.

EXAMPLE 5

A photoconductor was produced by forming a photosensitive layer in substantially the same manner as in example 3 except that 50 parts by weight of metal-free phthalocyanine, 100 parts by weight of the compound No. I-3 shown in Table 1, 50 parts by weight of a polyester resin (Vylon 200), and 50 parts by weight of PMMA were used to replace therewith the composition of the charge generating layer of Example 3.

EXAMPLE 6

A photoconductor was produced by forming a photosensitive layer in the same manner as in Example 5 except that the compound No. II-3 shown in Table 3 was used instead of the compound No. I-3 in Example 5.

EXAMPLE 7

A photoconductor was produced by forming a photosensitive layer in substantially the same manner as in Example 3 except that Chlorodiane Blue which is a bisazo pigment disclosed in, for example, Japanese Patent Laid-Open No. 37,543/1972 was used instead of metal-free phthalocyanine in the Example 3.

EXAMPLE 8

A photoconductor was produced by forming a photosensitive layer in the same manner as in Example 7 except that the compound No. II-2 shown in Table 3 was used instead of the compound No. I-2 in Example 7.

The electrophotographic characteristics of the photoconductors thus produced were measured by utilizing an electrostatic recording paper testing apparatus (Kawaguchi Denki Model SP-428).

The surface potential $V_s$ (volts) of each photoconductor is an initial surface potential which was measured when the surface of the photoconductor was positively charged in the dark by corona discharge at +6.0 kV for 10 seconds. After the discontinuation of the corona discharge, the photoconductor was allowed to stand in the dark for 2 seconds, after which the surface potential $V_d$ (volts) of the photoconductor was measured. Subsequently, the surface of the photoconductor was irradiated with white light at an illuminance of 2 luxes and the time (seconds) required for the irradiation to decrease the surface potential of the photoconductor to half of the $V_d$ was measured, then from which time and the illuminance the half decay exposure amount $E_{\frac{1}{2}}$ (lux.sec) was calculated. Also, the surface potential of the photoconductor after 10 seconds of irradiation thereof with white light at an illuminance of 2 luxes was measured as a residual potential $V_r$ (volts). When a phthalocyanine compound was used as a charge generating substance, a high sensitivity could be expected for light with longer wavelengths. Hence, the electrophotographic characteristics thereof were also measured by using a monochromatic light with a wavelength of 780 nm. Specifically, the $V_s$ and the $V_d$ of each photoconductor were measured in the same manner a described above, and the half decay exposure amount ($\mu J/cm^2$) was found by irradiation of the photoconductor surface with a monochromatic light (wavelength: 780 nm) of 1 μW instead of white light, while the residual potential $V_r$ (volts) was measured after 10 seconds of irradiation of the photoconductor surface with the above-mentioned light. The results of the measurements are shown in Table 5.

TABLE 5

| | White light | | | Light with wavelength of 780 nm | | |
|---|---|---|---|---|---|---|
| | $V_s$ volt | $V_r$ volt | $E_{\frac{1}{2}}$ lux·sec | $V_s$ volt | $V_r$ volt | $E_{\frac{1}{2}}$ μJ/cm$^2$ |
| 1 | 580 | 90 | 5.4 | 610 | 80 | 5.9 |
| 2 | 640 | 80 | 6.7 | 600 | 70 | 6.0 |
| 3 | 630 | 100 | 6.3 | 650 | 70 | 6.5 |
| 4 | 600 | 110 | 6.0 | 640 | 100 | 6.2 |
| 5 | 640 | 100 | 6.1 | 690 | 100 | 5.8 |
| 6 | 580 | 90 | 5.8 | 630 | 80 | 5.4 |
| 7 | 600 | 80 | 5.8 | — | — | — |
| 8 | 620 | 60 | 7.1 | — | — | — |

As can be seen in Table 5, the photoconductors of Examples 1 to 8 were not substantially different therebetween in the half decay exposure amounts and the residual potentials, and showed good surface potential characteristics. The photoconductors of Examples 1 to 6, using a phthalocyanine compound as the charge generating substance, showed also excellent electrophotographic characteristics for light with a long wavelength of 780 nm.

EXAMPLE 9

Selenium was deposited on an aluminum plate having a thickness of 500 μm by means of vacuum evaporation to form a charge generating layer having a thickness of 1.5 μm. A solution of 100 parts by weight of the hydrazone compound No. I-4 shown in Table 1 in 700 parts by weight of tetrahydrofuran (THF) was mixed with a solution of 100 parts by weight of polymethyl methacrylate (PMMA) in 700 parts by weight of toluene to prepare a coating liquid, which was then applied on the charge generating layer by the wire bar technique to form a charge transporting layer having a dry thickness of 20 μm. Thus, a photoconductor with the structure shown in FIG. 2 was produced. This photoconductor was charged by corona discharge at −6.0 kV for 0.2 second and examined with respect to electrophotographic characteristics to obtain good results, namely $V_s = -570$ V, $V_r = -40$ V and $E_{\frac{1}{2}} = 4.7$ lux.sec.

EXAMPLE 10

A photoconductor was produced by forming a photosensitive layer in the same manner as in Example 9 except that the compound No. II-4 shown in Table 3 was used instead of the compound No, I-4 in Example 9. The photoconductor thus produced was examined with respect to electrophotographic characteristics in the same manner as in Example 9 to obtain good result, namely $V_s = -600$ V, $V_r = -70$ V, and $E_{\frac{1}{2}} = 4.9$ lux.sec.

EXAMPLE 11

50 parts by weight of metal-free phthalocyanine treated n the same manner as in Example 3, and 50 parts by weight of a polyester resin (Vylon 200) were kneaded together with THF as a solvent with a mixer for 3 hours to prepare a coating liquid, which was then applied in an aluminum support to form a charge generating layer having a thickness of about 1 μm. Subsequently, 100 parts by weight of the hydrazone compound No. I-5 shown in Table 1, 100 parts by weight of a polycarbonate resin (Panlite L-1250, manufactured by Teijin Kasei Co., Ltd.), and 0.1 part by weight of a silicone oil were mixed with 700 parts by weight of THF and 700 parts by weight of toluene to prepare a coating liquid, which was then applied on the charge generating layer to form a charge transporting layer having a thickness of about 15 μm.

The photoconductor thus produced was charged by corona discharge at −6.0 kV for 0.2 second and examined with respect to electrophotographic characteristics in the same manner as in Example 9 to obtain good results, namely $V_s = -680$ V and $E_{\frac{1}{2}} = 5.3$ lux.sec.

EXAMPLE 12

A photoconductor was produced by forming a photosensitive layer in the same manner as in Example 11 except that the compound No. II-5 shown in Table 3 is used instead of the compound No. I-5 in Example 11. The photoconductor thus produced was examined with respect to electrographic characteristics in the same manner as in Example 11 to obtain good results, namely $V_s = -680$ V, and $E_{\frac{1}{2}} = 5.3$ lux.sec.

EXAMPLE 13

Photoconductors were produced by forming respective photosensitive layers in substantially the same manner as in Example 7 except the that the compounds Nos. I-6 to I-14 shown in Table 1, the compounds Nos. I-15 to I-28 shown in Table, 2, the compounds Nos. II-6 to II-13 shown in Table 3, and the compounds Nos. II-14 to II-26 shown in Table 4 were respectively used instead of the compound No. I-2. The results obtained by using the electrostatic recording paper testing apparatus (SP-428) are shown in Table 6.

Table 6 shows the half decay exposure amounts $E_{\frac{1}{2}}$ (lux.sec) obtained under the experimental conditions where the photoconductors were positively charged in the dark by corona discharge at +6.0 kV for 10 seconds and irradiated with white light at an illuminance of 2 luxes. The surface potential of the photoconductor after 10 seconds of irradiation with white light at an illuminance of 2 luxes was measured as a residual potential $V_r$ (volts).

TABLE 6

| Compound No. | $E_{\frac{1}{2}}$ (lux · sec) |
|---|---|
| I-6 | 5.8 |
| I-7 | 5.9 |
| I-8 | 7.3 |
| I-9 | 6.6 |
| I-10 | 7.5 |
| I-11 | 6.5 |
| I-12 | 6.7 |
| I-13 | 6.4 |
| I-14 | 5.4 |
| I-15 | 7.3 |
| I-16 | 5.9 |
| I-17 | 6.2 |
| I-18 | 6.8 |
| I-19 | 6.5 |
| I-20 | 8.9 |
| I-21 | 6.4 |
| I-22 | 6.3 |
| I-23 | 6.6 |
| I-24 | 7.2 |
| I-25 | 5.8 |
| I-26 | 6.3 |
| I-27 | 6.8 |
| I-28 | 7.2 |
| II-6 | 6.1 |
| II-7 | 7.3 |
| II-8 | 6.4 |
| II-9 | 8.9 |
| II-10 | 7.8 |
| II-11 | 6.5 |
| II-12 | 8.5 |
| II-13 | 7.3 |
| II-14 | 6.5 |

TABLE 6-continued

| Compound No. | $E_{\frac{1}{2}}$ (lux · sec) |
|---|---|
| II-15 | 7.3 |
| II-16 | 6.5 |
| II-17 | 5.2 |
| II-18 | 8.2 |
| II-19 | 7.3 |
| II-20 | 6.9 |
| II-21 | 6.7 |
| II-22 | 6.8 |
| II-23 | 6.9 |
| II-24 | 6.4 |
| II-25 | 5.9 |
| II-26 | 7.7 |

As can be seen in Table 6, the photoconductors using the compounds shown in the Table show good results with respect to the half decay exposure amounts.

According to the present invention, since a novel organic compound represented by any one of the aforementioned chemical formulae is used in a photosensitive layer formed on an electroconductive substrate, as a charge transporting substance, a photoconductor shows a high sensitivity and excellent characteristics in repeated use when adapted to either a positive charge mode or a negative charge mode. A suitable charge generating substance can be chosen so as to be adapted to the kind of exposure light source. By way of example, a phthalocyanine compound or a bisazo compound can be used as a charge generating substance to provide a photoconductor capable of being used in semiconductor laser printers. If necessary, a covering layer may be provided on the surface of a photoconductor to improve the durability thereof.

The invention has been described in detail with respect to preferred embodiments, and it will now be apparent from the foregoing to those skilled in the art that changes and modifications may be made without departing from the invention in its broader aspects, and it is the invention, therefore, in the appended claims to cover all such changes and modifications as fall within the true spirit of the invention.

What is claimed is:

1. A photoconductor for electrography comprising:
   a substrate; and
   a photosensitive layer formed on said substrate and including at least one organic compound represented by the following general formula (I) as a charge transporting substance:

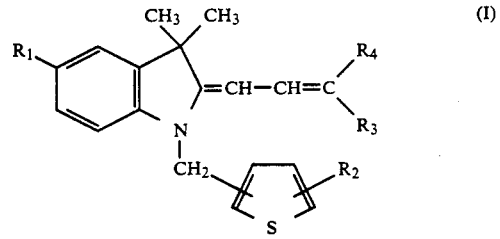

wherein, each of $R_1$ to $R_4$ stands for a hydrogen atom, a halogen atom, an alkoxy group, or an alkyl group, an aryl group, an alkenyl group, an aralkyl group, a thienyl group, each of which may have a substituent(s).

2. A photoconductor as claimed in claim 1, wherein said photosensitive layer comprises a layer including a dispersion of a charge generating substance and a charge transporting substance selected from the organic compounds represented by the general formulae (I) in a binder resin.

3. A photoconductor as claimed in claim 1, wherein said photosensitive layer comprises a laminate of a charge transporting layer including a charge transporting substance selected from the organic compounds represented by the general formulae (I) and a charge generating layer.

4. A photoconductor for electrophotography comprising:
   a substrate; and
   a photosensitive layer formed on said substrate and including at least one organic compounds represented by the following general formula (II) as a charge transporting substance:

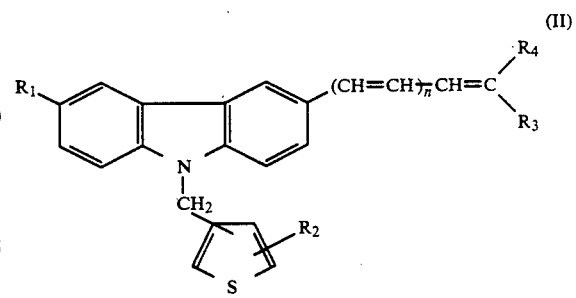

wherein, each of $R_1$ to $R_4$ stands for a hydrogen atom, a halogen atom, an alkoxy group, or an alkyl group, an aryl group, a thienyl group, an alkenyl group, an aralkyl group, each of which may have a substituent(s), n stands for an integer 0 or 1.

5. A photoconductor as claimed in claim 4, wherein said photosensitive layer comprises a layer including a dispersion of a charge generating substance and a charge transporting substance selected from the organic compounds represented by the general formulae (II) in a binder resin.

6. A photoconductor as claimed in claim 4, wherein said photosensitive layer comprises a laminate of a charge transporting layer including a charge transporting substance selected from the organic compounds represented by the general formulae (II) and a charge generating layer.

* * * * *